United States Patent [19]

Socci et al.

[11] 4,302,442

[45] Nov. 24, 1981

[54] NAIL ENAMELS

[75] Inventors: Robert Socci, Cedar Grove, N.J.; Anthony Gunderman, Winston Salem, N.C.; Eustace Fotiu, Mahwah, N.J.; Bernard Kabacoff, Norwalk, Conn.

[73] Assignee: USV Pharmaceutical Corporation, Tuckahoe, N.Y.

[21] Appl. No.: 217,623

[22] Filed: Dec. 18, 1980

Related U.S. Application Data

[63] Continuation-in-part of Ser. No. 79,949, Sep. 28, 1979, abandoned.

[51] Int. Cl.³ .............................................. A61K 7/04
[52] U.S. Cl. ............................... 424/61; 106/308 Q; 106/308 R
[58] Field of Search ............................................ 424/61

[56] References Cited

U.S. PATENT DOCUMENTS 2,383,990  9/1945  Quisling .................................. 424/61
3,422,185  1/1969  Kuritzkos ................................ 424/61
4,056,494  11/1977  Kronstein et al. ............... 106/308 Q

OTHER PUBLICATIONS

Miall, A New Dictionary of Chemistry, 1961, p. 316.

*Primary Examiner*—Dale R. Ore
*Attorney, Agent, or Firm*—Leon E. Tenenbaum; Ernest B. Lipscomb, III; Gilbert W. Rudman

[57] ABSTRACT

Migration of suspended materials in nail enamels is prevented by the addition thereto of from about 0.10 to 5.0% by weight of a phosphatide such as lecithin. Settling and migration of suspended materials in nail enamels is prevented by the addition thereto of from 0.10 to 5.0% by weight of a phosphatide such as lecithin and from about 0.04 to 0.20% by weight of a cosmetically acceptable acid.

12 Claims, No Drawings

NAIL ENAMELS

This application is a continuation-in-part of Patent Application Ser. No. 79,949 filed Sept. 28, 1979, now abandoned.

This invention relates to nail enamels. It particularly relates to nail enamels which are substantially free of the settling and the migration of the pigment and other materials suspended in the composition.

Conventional nail enamel compositions incorporate in their formulas a montmorillonite clay as a gellant to suspend pigments and pearlescent materials contained therein.

To achieve desired properties for these systems as much as 2.0% or more of the gellant is recommended to effect complete and stable suspension. The use of larger amounts of the gellant in a nail enamel composition adversely affects the application and flow properties of the preparation. When the levels of the gellant are reduced to about 0.5–1.25%, other additives must then be added to maintain desired suspension and performance characteristics. It is also known that nail enamel composition exhibit pigment migration, i.e., preferential separation, flocculation and flotation as distinguished from settling. While migration does not affect the performance of the nail enamel, the streaking effects noticeable from such migration are aesthetically undesirable.

The use of plant phosphatides, such as, for example, lecithins and the like, to avoid the difficulties in redispersing settled pigments of different specific gravities in paints has been reported in U.S. Pat. No. 4,056,494. However, the addition of lecithin to paints did not reduce the settling of the pigments.

It is, accordingly, an object of the present invention to provide means for preventing streaking effects in nail enamels, which occur on standing of said enamels.

It is another object of the present invention to provide means for substantially preventing the settling on standing of suspended materials in nail enamel compositions.

It is another object of the present invention to provide means for substantially preventing both standing and streaking effects which occur on standing in nail enamel compositions.

It is a further object of the present invention to provide nail enamel compositions which are substantially free of settling and streaking.

Other objects will appear from the description which follows.

In accordance with the present invention it has been found that the incorporation of from about 0.10% to 5.0% by weight of a phosphatide, such as, for example, lecithin, in nail enamel compositions will substantially prevent the migration (streaking) of suspended matter in nail enamels. It has also been found that the incorporation of from about 0.10% to 5.0% by weight of a phosphatide, such as, for example, lecithin, and from about 0.04% to 0.20% weight of a cosmetically acceptable acid in nail enamel compositions substantially prevents both the settling and migration (streaking) of the suspended matter in the nail enamel compositions. These desirable effects result from the combined action of the phosphatide and the acid since the incorporation alone of either the phosphatide or the acid does not prevent both the settling and the streaking. Preferably, about 0.66% weight of the phosphatide and about 0.05% weight of the acid are used.

While any animal or plant phosphatide is suitable for use in the nail enamel compositions of this invention, it is preferred to use a lecithin. Any lecithins are suitable, but hydroxy-lecithins are preferred. Of particular suitability is a hydroxylated lecithin supplied by the American Lecithin Co. of Woodside, N.Y., having the following properties:

| | |
|---|---|
| Acid value | 20–24 |
| pH at which 3% is dispersed | 6.6 |
| Iodine value | 82–85 |
| Benzene-insoluble material | 0.1–0.2% |
| Acetone-insoluble material | 60–62% |
| Moisture content | 1.57% |
| Color | 5 Gardner |

Any cosmetically acceptable acid which is compatible with nail enamel compositions may be used. These include phosphoric acid, sulfuric acid, citric acid, lactic acid, succinic acid, malic acid and the like. Malic acid and citric acid are preferred.

Table I illustrates the composition of several nail enamels prepared to contain varying amounts of the agents. In this table and Tables III and IV the numerical values refer to parts by weight.

Table II shows the evaluation of the compositions of Table I after standing for four (4) months at room temperature. In this table the numerals refer to the following ratings:

5.—Excellent—no visible signs of pigment migration or settling.

4.—Good—Very slight settling observed, no signs of pigment migration.

3.—Average—Some settling and very slight pigment migration.

2.—Poor—Settling and migration readily apparent (not saleable).

1.—Unacceptable—Very bad settling and migration (not saleable).

TABLE I

COMPOSITION OF THE NAIL ENAMEL

| Material | Composition No. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Nitrocellulose | 15.00 | 15.00 | 15.00 | 15.00 | 15.00 | 15.00 | 15.00 | 15.00 | 15.00 | 15.00 | 15.00 | 15.00 |
| Dibutyl Phthalate | 4.50 | 4.50 | 4.50 | 4.50 | 4.50 | 4.50 | 4.50 | 4.50 | 4.50 | 4.50 | 4.50 | 4.50 |
| Santolite Resin | 6.00 | 6.00 | 6.00 | 6.00 | 6.00 | 6.00 | 6.00 | 6.00 | 6.00 | 6.00 | 6.00 | 6.00 |
| Butyl Acetate | 30.00 | 30.00 | 30.00 | 30.00 | 30.00 | 30.00 | 30.00 | 30.00 | 30.00 | 30.00 | 30.00 | 30.00 |
| Ethyl Acetate | 8.00 | 8.00 | 8.00 | 8.00 | 8.00 | 8.00 | 8.00 | 8.00 | 8.00 | 8.00 | 8.00 | 8.00 |
| Toluene | 26.00 | 26.00 | 26.00 | 26.00 | 26.00 | 26.00 | 26.00 | 26.00 | 26.00 | 26.00 | 26.00 | 26.00 |
| Isopropanol | 7.50 | 7.50 | 7.50 | 7.50 | 7.50 | 7.50 | 7.50 | 7.50 | 7.50 | 7.50 | 7.50 | 7.50 |
| Bentone 27 | 1.00 | 1.00 | 1.00 | 1.00 | 1.00 | 1.00 | 1.00 | 1.00 | 1.00 | 1.00 | 1.00 | 1.00 |

TABLE I-continued

COMPOSITION OF THE NAIL ENAMEL

| Material | 1 | 2 | 3 | 4 | 5 | 6 | 7 | 8 | 9 | 10 | 11 | 12 |
|---|---|---|---|---|---|---|---|---|---|---|---|---|
| Malic Acid | — | 0.05 | — | — | — | — | — | — | 0.05 | 0.05 | 0.05 | 0.05 |
| Titanated Mica | 0.18 | 0.18 | 0.18 | 0.18 | 0.18 | 0.18 | 0.18 | 0.18 | 0.18 | 0.18 | 0.18 | 0.18 |
| Pigment | 0.60 | 0.60 | 0.60 | 0.60 | 0.60 | 0.60 | 0.60 | 0.60 | 0.60 | 0.60 | 0.60 | 0.60 |
| Hydroxylated Lecithin | — | — | 0.10 | 0.30 | 0.66 | 0.75 | 1.00 | 2.00 | 0.10 | 0.30 | 0.66 | 0.75 |

| Material | 13 | 14 | 15 | 16 | 17 | 18 | 19 |
|---|---|---|---|---|---|---|---|
| Nitrocellulose | 15.00 | 15.00 | 15.00 | 15.00 | 15.00 | 15.00 | 15.00 |
| DiButyl Phthalate | 4.50 | 4.50 | 4.50 | 4.50 | 4.50 | 4.50 | 4.50 |
| Santolite Resin | 6.00 | 6.00 | 6.00 | 6.00 | 6.00 | 6.00 | 6.00 |
| Butyl Acetate | 30.00 | 30.00 | 30.00 | 30.00 | 30.00 | 30.00 | 30.00 |
| Ethyl Acetate | 8.00 | 8.00 | 8.00 | 8.00 | 8.00 | 8.00 | 8.00 |
| Toluene | 26.00 | 26.00 | 26.00 | 26.00 | 26.00 | 26.00 | 26.00 |
| Isopropanol | 7.50 | 7.50 | 7.50 | 7.50 | 7.50 | 7.50 | 7.50 |
| Bentone 27 | 1.00 | 1.00 | 1.00 | 1.00 | 1.00 | 1.00 | 1.00 |
| Malic Acid | — | 0.05 | 0.10 | — | — | — | — |
| Pigment | 0.60 | 0.60 | 0.60 | 0.60 | 0.60 | 0.60 | 0.60 |
| Hydroxylated Lecithin | — | 0.50 | 0.50 | — | 0.50 | 0.50 | 0.50 |
| Citric Acid Monohydrate | — | — | — | 0.05 | 0.05 | 0.04 | 0.03 |

TABLE II

| Composition No. | Evaluation |
|---|---|
| 1 | 2 |
| 2 | 1 |
| 3 | 2 |
| 4 | 2 |
| 5 | 2 |
| 6 | 3 |
| 7 | 3 |
| 8 | 3 |
| 9 | 3 |
| 10 | 4 |
| 11 | 4 |
| 12 | 4 |
| 13 | 2 |
| 14 | 3 |
| 15 | 4 |
| 16 | 3 |
| 17 | 5 |
| 18 | 5 |
| 19 | 5 |

The addition of the hydroxylated lecithin to the nail enamel without the concomitant addition of an acid is effective in reducing the migration of the pigment. Table III shows the degree of streaking of different compositions of Table I which contain no acid, after standing for seven (7) days at 120° F.

TABLE IV

COMPOSITION OF THE NAIL ENAMEL

| | I | | II | | III | | IV | | V | | VI | | VII | |
|---|---|---|---|---|---|---|---|---|---|---|---|---|---|---|
| MATERIAL | A | B | C | D | E | F | G | H | I | J | K | L | M | N |
| NITROCELLULOSE | 15.00 | 15.00 | 15.00 | 15.00 | 15.00 | 15.00 | 15.00 | 15.00 | 15.00 | 15.00 | 15.00 | 15.00 | 15.00 | 15.00 |
| DBP | 4.50 | 4.50 | 4.50 | 4.50 | 4.50 | 4.50 | 4.50 | 4.50 | 4.50 | 4.50 | 4.50 | 4.50 | 4.50 | 4.50 |
| SANTOLITE RESIN | 7.50 | 7.50 | 7.50 | 7.50 | 7.50 | 7.50 | 7.50 | 7.50 | 7.50 | 7.50 | 7.50 | 7.50 | 7.50 | 7.50 |
| BUTYL ACETATE | 27.50 | 27.50 | 27.50 | 27.50 | 27.50 | 27.50 | 27.50 | 27.50 | 27.50 | 27.50 | 27.50 | 27.50 | 27.50 | 27.50 |
| ETHYL ACETATE | 14.00 | 14.00 | 14.00 | 14.00 | 14.00 | 14.00 | 14.00 | 14.00 | 14.00 | 14.00 | 14.00 | 14.00 | 14.00 | 14.00 |
| TOLUENE | 25.00 | 25.00 | 25.00 | 25.00 | 25.00 | 25.00 | 25.00 | 25.00 | 25.00 | 25.00 | 25.00 | 25.00 | 25.00 | 25.00 |
| ISOPROPYL ALCOHOL | 3.84 | 3.84 | 3.84 | 3.84 | 3.84 | 3.84 | 3.84 | 3.84 | 3.84 | 3.84 | 3.84 | 3.84 | 3.84 | 3.84 |
| BENTONE 27 | 1.00 | 1.00 | 1.00 | 1.00 | 1.00 | 1.00 | 1.00 | 1.00 | 1.00 | 1.00 | 1.00 | 1.00 | 1.00 | 1.00 |
| MALIC ACID | 0.05 | 0.05 | 0.05 | 0.05 | 0.05 | 0.05 | 0.05 | 0.05 | 0.05 | 0.05 | 0.05 | 0.05 | 0.05 | 0.05 |
| NATURAL PEARL | 0.37 | 0.37 | 0.37 | 0.37 | 0.37 | 0.37 | 0.37 | 0.37 | 0.37 | 0.37 | 0.37 | 0.37 | 0.37 | 0.37 |
| PIGMENT | 0.36 | 0.36 | 0.28 | 0.28 | 0.15 | 0.15 | 0.05 | 0.05 | 0.24 | 0.24 | 0.31 | 0.31 | 0.46 | 0.46 |
| IRON BLUE | 0.007 | 0.007 | 0.02 | 0.02 | 0.02 | 0.02 | 0.001 | 0.001 | 0.02 | 0.02 | 0.01 | 0.01 | 0.01 | 0.01 |
| BROWN IRON OXIDE | 0.13 | 0.13 | 0.26 | 0.26 | 0.35 | 0.35 | 0.02 | 0.02 | 0.35 | 0.35 | 0.20 | 0.20 | 0.21 | 0.21 |
| TiO₂ | 0.23 | 0.23 | 0.15 | 0.15 | 0.40 | 0.40 | — | — | 0.01 | 0.01 | 0.50 | 0.50 | 0.41 | 0.41 |
| HYDROXYLATED LECITHIN | — | 0.66 | — | 0.66 | — | 0.66 | — | 0.66 | — | 0.66 | — | 0.66 | — | 0.66 |

TABLE V

| Composition No. | Evaluation |
|---|---|
| I-A | 1 |
| I-B | 5 |
| II-C | 2 |
| II-D | 4.5 |
| III-E | 2 |
| III-F | 5 |
| IV-G | 1.5 |
| IV-H | 4.5 |
| V-I | 3 |
| V-J | 4.5 |
| VI-K | 2 |
| VI-L | 4.5 |
| VII-M | 3 |
| VII-N | 4.5 |

The results, as shown in Tables II and V, clearly indicate the superior properties in respect of settling and migration in nail enamel compositions containing both hydroxylated lecithin and malic acid, and the results, as shown in Table III, clearly indicate the effect of addition of hydroxy lecithin in reducing the migration (streaking) in nail enamels.

The compositions according to the present invention contain from about 0.04% to 0.2% by weight of a cosmetically acceptable acid and from about 0.10% to 2.0% by weight of lecithin in a nail enamel which is comprised of a nail enamel base and one or more desired pigments. Nail enamel bases suitable for the compositions of the present invention are usually comprised of nitrocellulose, plasticizer, resin, solvent, and suspending agent. The resin may, if desired, be omitted. Examples of such suitable bases are described in Cosmetics, Science and Technology: Balsam and Sagarin, Editors, Second Edition 1972, Volume 2, Chapter 29, Wiley-Interscience, New York.

The preferred compositions contain in weight percent:

| Nail Base | 96–99 |
|---|---|
| Pigment | 0.5–2.0 |
| Cosmetically acceptable acid | 0.04–0.2 |
| Lecithin | 0.10–2.0 |

Example 1 shows the composition of a suitable nail enamel composition according to the present invention. In this example the numerical values refer to parts by weight.

| nitrocellulose | 15.5 |
|---|---|
| dibutyl phthalate | 4.5 |
| resin | 7.5 |
| butyl acetate | 27.0 |
| ethyl acetate | 14.0 |
| toluene | 25.00 |
| isopropanol | 3.84 |
| suspending agent | 1.00 |
| malic acid | 0.05 |
| hydroxy-lecithin | 0.66 |
| pigment | 1.50 |

We claim:

1. In a method for substantially preventing the migration of suspended materials in nail enamels, the improvement comprising the addition of from about 0.10 to 5.0% by weight of a hydroxylated lecithin to said nail enamels.

2. A method according to claim 1 wherein the hydroxylated lecithin has the following properties:

| acid value | 20–24 |
|---|---|
| pH at which 3% is dispersed | 6.6 |
| iodine value | 82–85 |
| benzene-insoluble material | 0.1–0.2% |
| acetone-insoluble material | 60–62% |
| moisture content | 1.57% |
| color | 5 Gardner |

3. In a method for substantially preventing the settling and migration of suspended materials in nail enamels the improvement comprising the addition to the nail enamels of about 0.10 to 5.0% by weight of a hydroxylated lecithin and from about 0.04 to 0.20% by weight of a cosmetically acceptable acid.

4. A method according to claim 3 wherein the hydroxylated lecithin has the following properties:

| acid value | 20–24 |
|---|---|
| pH at which 3% is dispersed | 6.6 |
| iodine value | 82–85 |
| benzene-insoluble material | 0.1–0.2% |
| acetone-insoluble material | 60–62% |
| moisture content | 1.57% |
| color | 5 Gardner |

5. A method according to claim 4 wherein the acid is selected from the group consisting of phosphoric acid, sulfuric acid, citric acid, succinic acid and malic acid.

6. A method according to claim 5 wherein the acid is malic acid.

7. A method according to claim 5 wherein the acid is citric acid.

8. A method according to claim 6 wherein the composition contains about 0.66% weight of the hydroxylated lecithin and 0.05% weight of malic acid.

9. A method according to claim 7 wherein the composition contains about 0.50% weight of the hydroxylated lecithin and about 0.05% weight citric acid.

10. In a nail enamel which is substantially free from settling and migration of suspended materials contained therein, the improvement comprising said nail enamel containing from about 0.04 to 0.2% by weight of a cosmetically acceptable acid and from about 0.10 to 2.0% by weight of a hydroxylated lecithin in said nail enamel.

11. A nail enamel according to claim 10 wherein the cosmetically acceptable acid is malic acid or citric acid.

12. A nail enamel according to claim 11 wherein the hydroxylated lecithin has the following properties:

| acid value | 20–24 |
|---|---|
| pH at which 3% is dispersed | 6.6 |
| iodine value | 82–85 |
| benzene-insoluble material | 0.1 to 0.2% |
| acetone-insoluble material | 60 to 62% |
| moisture content | 1.57% |
| color | 5 Gardner |

* * * * *